United States Patent [19]

Bergersen

[11] 4,073,061
[45] Feb. 14, 1978

[54] CLOSELY ADAPTED ORTHODONTIC APPLIANCE

[76] Inventor: Earl Olaf Bergersen, 950 Linden Ave, Winnetka, Ill. 60093

[21] Appl. No.: 695,103

[22] Filed: June 11, 1976

[51] Int. Cl.² ............................................. A61C 7/00
[52] U.S. Cl. ................................................. 32/14 B
[58] Field of Search ...................... 32/14 B, 14 A, 2; 128/136

[56] References Cited

U.S. PATENT DOCUMENTS

| | | | |
|---|---|---|---|
| 3,379,193 | 4/1968 | Monaghan | 128/136 |
| 3,411,501 | 11/1968 | Greenberg | 128/136 |
| 3,898,736 | 8/1975 | Bergersen | 32/14 B |
| 3,924,638 | 12/1975 | Mann | 128/136 |

*Primary Examiner*—Robert Peshock
*Attorney, Agent, or Firm*—Larson, Taylor and Hinds

[57] ABSTRACT

An orthodontic appliance closely adapted to a patient's teeth for holding the same securely in place and a method for forming the same. A preform having a trough formed between a labial-buccal flange and a lingual flange is designed preferably for only one of the upper or lower row of teeth. It is formed of a material which is quite hard, i.e. essentially non-resilient, and it has the property of becoming soft for non-elastic reshaping at a temperature above body temperature and below 212° F. The preform is heated and when soft it is placed within the patient's mouth and reshaped to precisely the contour of at least some if not all of the teeth of the row to which it is applied. The appliance is then cooled, preferably while still in the patient's mouth, after which the flanges are preferably trimmed back to the gum line and even beyond that for the portion of the labial-buccal flange against the labial surfaces of the anterior teeth.

36 Claims, 14 Drawing Figures

CLOSELY ADAPTED ORTHODONTIC APPLIANCE

BACKGROUND OF THE INVENTION

This invention relates to the orthodontic treatment of teeth, and in particular it relates to an orthodontic appliance for holding teeth in a selected position, and to a method for forming the appliance.

In the field of orthodontics, conventional orthodontic devices such as bands or the like are often used for straightening teeth to bring them to a predetermined position of proper or close to proper occlusion. To bring teeth into a final position of desired orientation in the mouth, the orthodontist will often use any one of a number of different appliances including for example a Hawley device or a positioner, for example either a preformed positioner as described in my previous U.S. Pat. No. 3,898,736 or a custom made positioner as described in the Kesling U.S. Pat. No. 2,467,432.

Whichever appliance or combination of appliances are used, at one or more different times throughout the treatment process, and in particular at the end of the treatment process, the orthodontist wishes merely to maintain the teeth in a certain fixed position. The difficulty is that during the treatment process, i.e. as the teeth are being moved to different positions, the tissues tending to hold the teeth in any given position are somewhat weakened, as a result of which, whenever appliances are removed there is a strong tendency for a relapse, i.e. for the teeth to retreat to an earlier position rather than remain in the new position to which they have been moved. Therefore, there exists a need for a means which can be applied to a patient's teeth promptly after removal of any of the usual orthodontic appliances for positively holding the patient's teeth in a given selected position.

SUMMARY OF THE INVENTION

Thus, it is a purpose of the present invention to provide an improvement in orthodontic treatment which will solve the problem of the prior art by providing a way to hold a patient's teeth in any selected position.

This purpose of the present invention is achieved by providing an orthodontic appliance adapted to be shaped directly within the patient's mouth to form a retainer like appliance of the type which is generally U-shaped in plan view and includes a trough formed between a labial-buccal flange and a lingual flange, which trough exactly fits the row of teeth, i.e. either the upper or the lower row of teeth to which it is applied. The appliance is of a relatively hard material (such as that used to form a Hawley retainer), which material has the characteristic of softening at an elevated temperature which is not uncomfortable in the patient's mouth so that the appliance can be heated up and hence softened and then non-elastically reshaped directly within the patient's mouth, and then permitted to cool. The result is an appliance which exactly fits a row of the patient's teeth over most of the clinical crown surface of the teeth of that row and which is of the said hard material. Consequently, the appliance has the characteristic of actually snapping into place on the patient's teeth to be retained thereon during use and to precisely match the shape and position of the teeth at that moment so as to hold the teeth in that position.

In accordance with a preferred arrangement, the appliance of the present invention would initially be provided prior to reshaping in the mouth as a preform which, aside from being of a hard material would generally resemble a positioner of the type described in my previous U.S. Pat. No. 3,898,736, but with only one trough for one row of teeth (separate upper and lower preforms would be provided) and including depressions within the trough generally corresponding to the patient's teeth. Moreover, to facilitate providing a preform most closely adapted to the general shape of a patient's teeth even before reshaping thereof, the preforms would preferably be provided in a plurality of different sizes so that the orthodontist could select a preform closely approximating the shape of the row of teeth to which the appliance is to be provided, thereby minimizing the extent to which the appliance must actually be physically reshaped when applied to the patient's teeth.

In accordance with a preferred procedure for forming a finished appliance of the present type, the orthodontist would first select a preform closest to the shape of the patient's teeth and then heat the preform to its softening temperature and while soft place it in the patient's mouth and reshape it to the exact shape of the row of teeth to which it is applied. The appliance would then be permitted to cool, preferably while still within the patient's mouth, until it became somewhat stiff. The appliance would then be removed and the flanges would be trimmed back to the patient's gum line and even farther adjacent the labial surfacs of the anterior teeth.

With the present invention, there is therefore provided an appliance which can be virtually instantaneously shaped to the exact shape of a patient's teeth, thereby providing the orthodontist with the opportunity of assuring that the patient's teeth are held in any given position almost immediately after removal of other conventional orthodontic devices. Consequently, an opportunity for relapse is eliminated since with this appliance there can be no tooth rotations or individual tooth movements. Cooperation due to its closeness of fit would also be increased.

The appliance is also capable of being made in accordance with a number of modifications. For example, the labial-buccal flange can be modified to include either hooks for receiving an elastic band or a labial wire of the type used in a Hawley retainer. Also, since the appliance of the present invention is relatively hard and closely adapted to the teeth, it is contemplated that for patient comfort, it would only be made for one row of teeth at a time (although theoretically it could be made with both an upper and a lower tooth receiving trough). Consequently, separate upper and lower appliances could be provided with suitable means such as projection and socket means for temporarily and removeably securing the upper and lower appliances together for short term use as a single unit.

Thus, it is an object of the present invention to provide improvements in orthodontic treatment which will permit retaining a patient's teeth in any given position to prevent relapse thereof.

It is another object of this invention to provide an orthodontic appliance capable of being applied to a patient's teeth and exactly adapted to the shape and position of the patient's teeth almost immediately upon removal of other orthodontic devices and to a method for forming the same.

It is still another object of this invention to provide an orthodontic appliance of a hard material capable of being softened at an elevated temperature for reshaping directly within a patient's mouth to precisely fit the contours of the clinical crown surfaces of a patient's teeth such that after it cools down and becomes hard, it can be immediately snapped into place on the patient's teeth to retain the teeth in that position.

It is still another object of this invention to provide a method for forming a dental appliance by providing a preform of relatively hard material, heating the preform to a softening temperature, placing the preform within the patient's mouth while it is soft and reshaping the preform while in this state to precisely the shape of the patient's teeth, and then permitting the preform to cool and become hard again, and trimming the flanges of the appliance, preferably back to the gum line or gingival edges of the teeth.

It is still another object of the present invention to provide a set of a limited number of preforms adapted to be formed into an appliance of the type referred to herein, such that the orthodontist can select a preform closely approximating the shape of the patient's row of teeth before heating and reshaping that appliance to precisely fit the patient's teeth.

Other objects and advantages of the present invention will become apparent from the detailed description to follow, together with the accompanying drawings.

BRIEF DESCRIPTION OF THE DRAWINGS

There follows a detailed description of a preferred embodiment of the invention to be read together with the accompanying drawings in which.

DETAILED DESCRIPTION OF THE PREFERRED EMBODIMENTS

Figure 1:
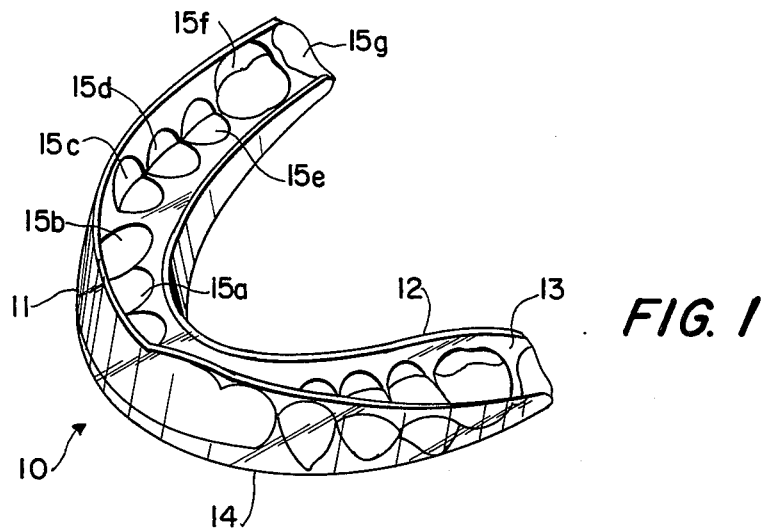
FIG. 1 is a perspective view of a preform of an orthodontic appliance made in accordance with the present invention and adapted for use with only the upper row of teeth.

Referring now to the drawings, like elements are represented by like numerals throughout the several views.

FIG. 1 illustrates a preform of an orthodontic appliance adapted for use in accordance with the present invention. In outward appearance, it resembles an orthodontic positioner of the type shown and described in my U.S. Pat. No. 3,898,736, but constructed for only the upper row of teeth. In this regard it includes a labial-buccal flange 11, a lingual flange 12, and a trough 13 formed between these flanges and having formed therein depressions corresponding generally to the position of the patient's teeth. The right hand depressions for the right side of the patient's upper teeth are designated 15a through 15g and correspond to the patient's teeth, 15a adapted for the patient's right central incisor, 15b the right lateral incisor, 15c through 15e the cuspid and bicuspid teeth and the remainder for the patient's molar teeth. The bottom of this preform is generally flat and plain and is represented generally by the numeral 14.

The appliance 10 differs from such a positioner, however, in several respects. Firstly, the preform 10 is formed of a very hard, stiff material as contrasted to the soft resilient material of an orthodontic positioner. The reasons for this will become more apparent below. In addition, the flanges 11 & 12 extend upwardly only as far as the gingival edges of the teeth, i.e. the gum line. There is no need to extend these flanges farther since the preferred procedure for carrying out the present invention is to trim back the flanges on the finished appliance such that the flanges extend away from the occlusal edges of the teeth no farther than the gingival edges thereof, i.e. they cover no more than the clinical crown portion of the teeth and do not cover the gum or periodontal tissues.

Figure 2:
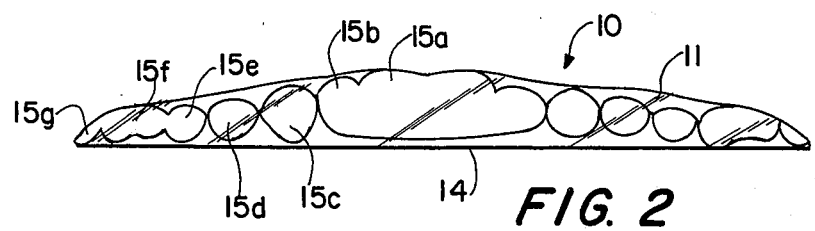
FIG. 2 is a front elevational development view of FIG. 1.

The front elevational development view of FIG. 2 further illustrates the height of the labial-buccal flange 11 relative to the tooth receiving depressions within the trough 13.

Figure 3:
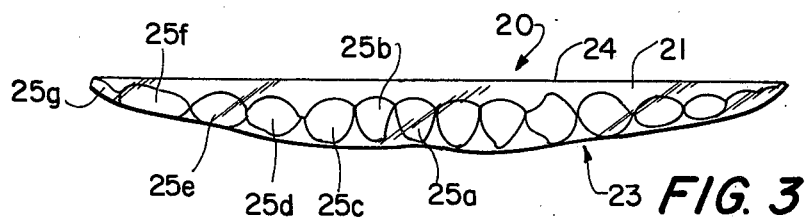
FIG. 3 is a front elevational development view of a preformed orthodontic appliance of the type as shown in FIGS. 1 & 2, but for the lower row of teeth.

A mandibular preform for the lower teeth would be quite similar to the preform shown in FIG. 1 except that it would be turned over and the depressions would of course be arranged differently since they would be adapted for the somewhat differently shaped and arranged lower teeth. Therefore, the preform for the lower teeth is shown only in front elevational development view in FIG. 3 wherein there is shown a mandibular preform 20 having a labial-buccal flange 11 forming with a lingual flange (not shown) a trough 23 having tooth receiving depressions 25a through 25g therein, which depressions correspond generally to depressions 15a through 15g of FIG. 1 except of course that they are for the lower teeth.

It is these preforms which would be supplied to the practicing orthodontist. In a manner to be described in greater detail below, the orthodontist would then adapt the preforms to the shape of a specific patient's teeth for holding those teeth in a certain selected position. However, before explaining this procedure in detail, it would be helpful to further describe certain aspects of the preforms.

Firstly, to carry out the basic purposes of the invention, it is necessary that the preforms be made of a material which is quite hard at the temperature of use, i.e.

body temperature, and concurrently capable of being softened at a temperature sufficiently above body temperature so that it will not inadvertently become soft in use by the patient, and concurrently not too high that it will injure the patient's mouth so that in its softened state it can be placed into the patient's mouth for manipulation thereof. A suitable temperature for such softening is approximately 175° F although the invention can be carried out with softening temperatures just slightly above body temperature such as 100° F and at the upper end of the range, the softening temperature would not be above 212° F since it will preferably be softened in hot water. In practice, however, it is believed that the softening range would preferably be between 115° and 200° F.

Thermoplastic materials have been found quite successful for the purpose of the present invention. Two such thermoplastics are copolymers of vinyl-chloride - vinyl acetate and methyl methacrylate - ethyl acrylate.

A suitable composition is 85 – 100% of a vinyl-chloride - vinyl acetate copolymer and from 0–15% of a polyester type plasticizer. The composition may be prepared by any of the numerous plasticization techniques such as that disclosed in Bilmeyer, Testbook of Polymer Science at page 414. However, it should be noted that this is just a preferred material and it will be apparent that the purposes of the present invention, as described and claimed herein, can be achieved with other materials having similar properties.

Since the orthodontic appliance of the present invention is to be reshaped within the patient's mouth, then from a theoretical point of view, the shape of the preform prior to reshaping would not be important. In a theoretical sense, this is true; and if in fact there could be provided a material which was perfectly hard at room temperature and which was very, very soft at its softening temperature, then perhaps total reshaping from a blob of material would be possible, However, within the limitations of existing materials, for example, the materials as described above, the softness achieved at the softening temperature is not absolute so that in a practical sense it is important that the preform closely approximate the shape of the patient's teeth before reshaping so as to minimize the extent of required reshaping. In the present preferred arrangement, the preform not only resembles the general U-shaped configuration, but in addition it already includes depressions therein approximating the shape of the patient's teeth. To further approximate the shape of the preform to the patient's teeth, the preforms are provided in a plurality of sizes. For example, as will be described in greater detail below, it is preferable to provide the orthodontist with eleven different sizes for each of the upper and lower row of teeth merely for the non-extraction situation and eleven further sizes for each of the upper and lower row of teeth for four bicuspid extraction, and nine sizes for upper bicuspid only extraction cases, these being provided for both the upper and lower rows of teeth. In total, these preforms would then come preferably in 62 sizes, 31 for the upper row and 31 for the lower row of teeth.

The orthodontist would now use and form the appliance of the present invention as follows. The appliance might be used in at least the following three situations. Firstly, following the use of a positioner, for example a positioner of the type shown in my U.S. Pat. No. 3,898,736, or a custom made positioner as shown for example in the Kesling U.S. Pat. No. 2,775,036 for approximately three to four weeks to completely position the teeth into their final positions after the removal of all orthodontic appliances. This new snap-on appliance is then adapted to the teeth and if worn each night and also days if required, it will hold the teeth in the place that the positioner has placed them. Secondly, this appliance may be applied directly following the removal of all orthodontic appliances, wherein this snap-on appliance would be adapted and worn either all the time or half the time at nights for an indefinite period of time (usually for two years). Thirdly, the appliance could be used directly following the initial closure of band spaces by either an elastic from one molar around to the other molar or by tying back the arch while only the molar bands are left in the mouth. The snap-on appliance of the present invention would then be adapted to the teeth to hold them in position. The appliance would have the advantage of absolutely holding each tooth exactly where it had been placed either by the orthodontic appliance or by the positioner. As long as this type of appliance is being worn, there will be no rotations or individual tooth movements. Cooperation due to its closeness of fit would be increased.

In practice, the orthodontist, at whatever time he selects for use of the present invention would first of all select a preform of the proper size for his patient. Selection of the proper size could be accomplished by measuring the patient's anterior teeth in the manner as described in my said U.S. Pat. No. 3,898,736. With the proper size preform, the orthodontist would then heat the preform to its softening temperature which would be in the range as described above and would preferably be in the neighborhood of 175° F. At this time the orthodontist would place the preform into the patient's mouth onto the teeth while the material is in the softened piable state. The orthodontist would then firmly manipulate the preform so that the interior of the trough became precisely and exactly adapted to the shape of the patient's teeth, and preferably to the entire clinical crown surface (the exposed white enamel portion) of all of the patient's teeth of the row of teeth to which the appliance is being applied. It will be appreciated that approximately half of the clinical crown surface of all teeth closest to the gingival edges thereof which is known as the "undercut portion" of those teeth tends to be of reduced cross-sectional area relative to portions located occlusally thereof. Therefore, as the material of the appliance becomes closely adapted to these undercut areas of smaller cross-section, then it will be apparent that after the material hardens the said larger cross-sectional portions of the teeth will offer a resistance to movement of the appliance off of the teeth. This will therefore provide the "snap-on" feature of the appliance made in accordance with the present invention.

After the appliance has been reshaped to the patient's teeth, it is allowed to cool and become slightly stiff, preferably while still in the patient's mouth, after which it is removed and becomes completely stiff, i.e. essentially nonresilient. The flanges are then trimmed back to the gum line, and beyond the gum line in the area of the anterior teeth. For the upper teeth, the labial flange is preferably trimmed back to approximately one-third the height of the clinical crown surfaces of these teeth (i.e. cuspids, lateral incisors and central incisors). For the lower appliance, the labial flange would be trimmed back preferably to half of the exposed clinical crown surfaces of the lower anterior teeth. The reason for the additional trimming for the labial surfaces of the anterior teeth is primarily for patient comfort since it minimizes interference of the appliance with the front interior of the mouth. Also, there is sufficient contact between the interior of the appliance and the teeth in other areas so that the appliance will stay in place on the teeth even without this complete contact with the anterior teeth.

Figure 9:
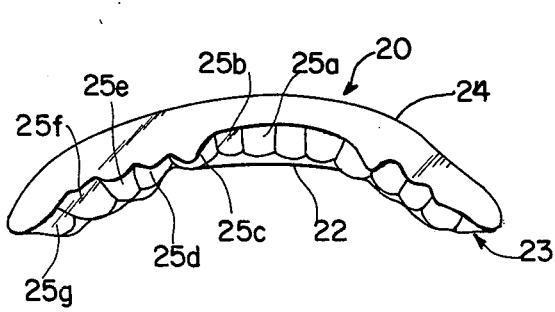
FIG. 9 is a front perspective view of an orthodontic appliance of the type shown in FIG. 3 for the lower teeth after it has been adapted for a specific patient.
Figure 10:
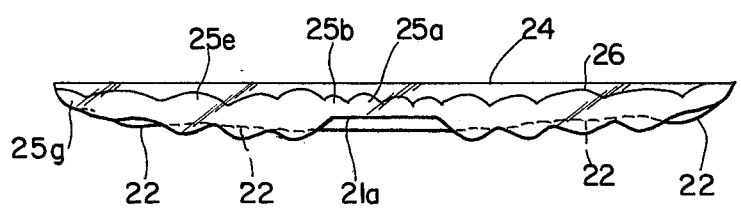
FIG. 10 is a front elevational development view of FIG. 9.
Figure 11:
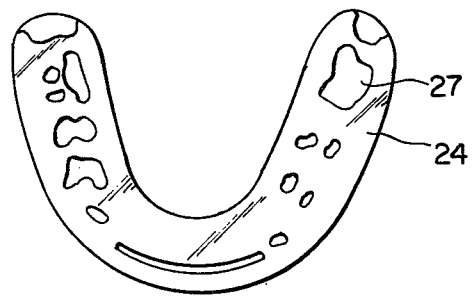
FIG. 11 is a bottom view of the appliance of FIGS. 9 & 10.

FIGS. 4 through 8 illustrate an appliance after it has been formed to the shape of a specific patient's upper row of teeth and after the flanges 11 and 12 have been trimmed back to the gum line and the labial-buccal flange has been further trimmed back at 11a in the area of the upper anterior teeth. FIGS. 9 through 11 correspond to FIGS. 4 through 6 except that they show an appliance adapted to fit a patient's lower row of teeth. In FIG. 10, 21a represents the additional trimming back of the labial-buccal flange 21 in the vicinity. of the lower anterior teeth.

Figure 6:
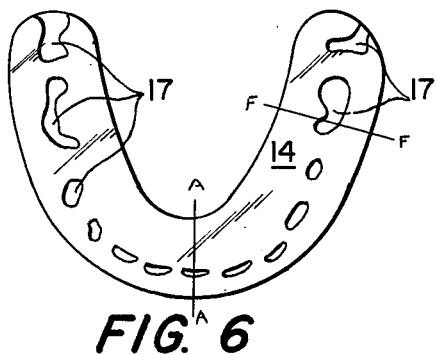
FIG. 6 is a bottom view of the appliance shown in FIGS. 4 & 5.
Figures 7, 8:
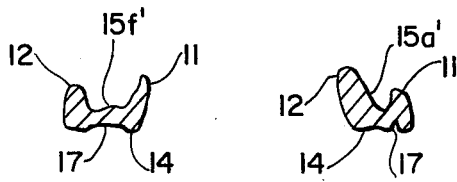
FIG. 7 is a cross-sectional view taken in a plane represented by the line F—F of FIGS. 4 & 6.
FIG. 8 is a cross-sectional view taken in a plane represented by the line A—A in FIGS. 4 & 6.

FIGS. 6 and 11 illustrate the outer side of the upper and lower appliance, respectively, i.e. the side engaging the occlusal surfaces of the other row of teeth. Referring to FIG. 6, if this lower surface were completely planer, then the occlusal surfaces of some lower teeth would engage this surface before others, thereby limiting the abiliby to close the lower teeth against this surface. This would constitute a rather uncomfortable situation as compared with the desirable situation whereby all occlusal surfaces contact this surface 14 essentially concurrently. To achieve the desired result, while the preform is in its soft state and is being formed within the patient's mouth, the patient is asked to move the lower teeth up into the surface 14, whereby the first teeth to engage will move slightly into this surface, and so on until the last teeth to engage barely engage this surface. As a result, there will be formed in surface 14 a random pattern corresponding to the uppermost surfaces of the lower teeth. These indentations will therefore provide a somewhat haphazard pattern as represented by the numeral 17 in FIG. 6. These indentations are also shown in part in FIGS. 7 and 8.

FIG. 11 illustrates the opposite of FIG. 6, i.e. the upper surface of the lower appliance wherein the haphazard arrangement of impressions 27 in the otherwise plain surface 24 receives the occlusal surfaces of the upper teeth so that the upper teeth close onto the surface 24 essentially concurrently with each other.

Figure 12:
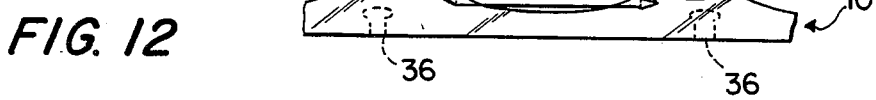
FIGS. 12 & 13 are partial front elevational views similar to FIGS. 5 & 10, respectively, and showing modifications of the present invention.
Figure 13:
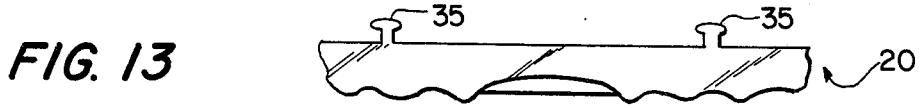
Figure 14:
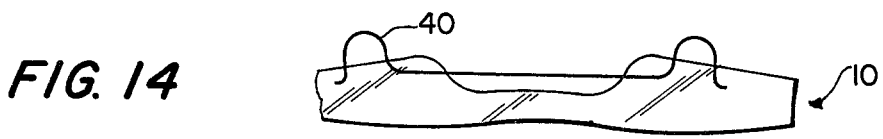
FIG. 14 is a partial front perspective view similar to FIG. 12 and showing an additional modification of the present invention.
Figure 4:
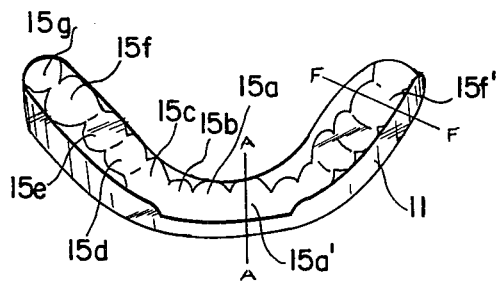
FIG. 4 is a front perspective view of the appliance of FIG. 1 after it has been adapted for a specific patient.
Figure 5:
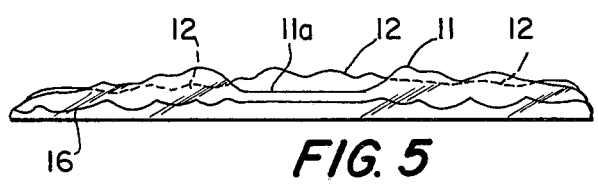
FIG. 5 is a front elevational development view of FIG. 4.

FIGS. 12 through 14 illustrate some modifications of the present invention. Referring to FIG. 12, there may be provided on the labial flange 11 a pair of hooks 30 for receiving a suitable elastic band 31. The hooks may be an intrigual part of the material of the appliance or they might be formed from metal prongs or the like embedded in and projecting out from the material of flange 11.

The purpose of the band 31 would be to apply pressure to the exposed portions of the anterior teeth to exert a pressure thereon tending to close certain spaces therebetween.

FIGS. 12 and 13 taken together illustrate still another modification. It may be desirable on occasion to resiliently and removeably secure the upper and lower appliances 10 and 20 together. For this purpose, one of the appliances may be provided with projections such as 35, and the other may be provided with suitable sockets such as 36, which may be adapted to resiliently and firmly but removeably receive the projections 35.

Further, the appliance of the present invention may also have formed in combination therewith a labial wire as shown at 40 in FIG. 14 for engaging and acting upon the anterior teeth.

In a preform of the present type, the isthmus, i.e. the material between the bottoms of the tooth receiving depressions and the opposite plain surface 14 or 24 would normally have a thickness of between 2mm in the posterior region and it would get progressively thicker towards the front and would be about 3 mm in the front.

As explained above, the preforms preferably come in a number of sizes so that the appliances roughly approximate the shape of the patient's teeth even before reshaping, thereby facilitating the task of reshaping the appliance to the patient's teeth and providing much greater leeway with respect to selection of materials. In accordance with a perferred arrangement of the present invention, these preforms would be supplied in the following sizes in which there are provided a total of forty-four sizes, including eleven sizes for an upper non-extraction retainer, eleven sizes for a lower non-extraction retainer, eleven sizes for an upper extraction retainer, and eleven sizes for a lower extraction retainer. As is known in the art, "extraction" refers to the situation wherein to reduce crowding, the orthodontist removes four bicuspid teeth as part of the treatment process. The dimensions for the non-extraction retainers (upper and lower) are given in the Tables I and III below, and the dimensions for the extraction retainers (upper and lower) are given in Tables II and IV below. A set of retainers made according to these dimensions will fit substantially the entire orthodontic patient population although as noted above, other sizes could be provided for special cases. For example when combining an extraction upper with a non-extraction lower, or vice versa, the sizes would be essentially the same as given in the Tables I to IV, although the means for removably connecting the upper and lower retainers may have to be in a slightly different location then when using an upper and lower pair of the same type.

DEFINITIONS OF DIMENSIONS TABLES I AND II (for both upper and lower)
a. Greatest anterior vertical height (labial flange).
b. Vertical height through first pre-molar area (buccal-flange).
c. Vertical height through the first molar area in line with the center of mesio-buccal cusp of the upper molar (buccal-flange).
d. Vertical height through the midline on the anterior surface (labial flange).
e. Gross length of the appliance through the midline to the line perpendicular to it running tangent across the most posterior extents of the appliance.
f. Greatest width through the molar area.
g. Distance between lingual flanges at level of mesio-lingual cusps of the first permanent molars.
h. Width through the middle of the first molar area.
i. Width through the middle of the first pre-molar area.
j. Width through the mesial of the central incisors.
k. Height of the lingual flange at the midline.
l. Height of the lingual flange through the first pre-molar area.
m. Height of the most distal portion of the flange mid-way between the buccal and lingual cusps of the first molar.
n. Height of the flange of the upper retainer from the incisal edge to the -continued DEFINITIONS OF DIMENSIONS TABLES I AND II (for both upper and lower)
flange (in the upper arch).
o. Height of the flange of the lower retainer from the incisal edge of the lower central incisor to the edge of the margin of the retainer.
p. Height of the flange of the upper retainer from the tip of the cusp of the upper canine to the margin of the retainer.
q. Height of the flange of the lower retainer from the tip of the lower cusp of the canine to the margin of the retainer.
r. Height of the flange of the upper retainer from the tip of the mesio-buccal cusp to the edge of the margin of the retainer.
s. Height of the flange of the lower retainer from the tip of the mesio-buccal cusp of the lower first molar to the margin of the retainer.
t. Distance ("freeway space") at the midline from the tip of the incisal edge of the upper or lower central incisor to the occlusal surface of the retainer.
v. Free-way space at leval of mesio-buccal cusp of first molar.
w. Fee-way space at leval of first bicuspid (or second in extraction cases).
x. Free-way space at leval of canine.

TABLE I

GROSS DIMENSIONS FOR CLOSELY ADAPTED RETAINER
Non-Extraction
in m.m.

| Size | | a | b | c | d | e | f | g | h | i | j | k | l | m | n | o | p | q | r | s | t | v | w | x |
|---|---|---|---|---|---|---|---|---|---|---|---|---|---|---|---|---|---|---|---|---|---|---|---|---|
| 1 | Upp | 3.4 | 7.2 | 5.0 | 3.4 | | | | | | | 4.9 | 4.1 | 1.0 | | | | | | | | | | |
| | | | | | | 35.4 | 53.2 | 22.5 | 14.3 | 13.6 | 11.4 | | | | 2.0 | 5.4 | 7.1 | 6.1 | 4.3 | 2.6 | 1.4 | 0.7 | 0.9 | 1.0 |
| | Low | 6.8 | 4.8 | 3.3 | 6.8 | | | | | | | 4.9 | 4.1 | 1.0 | | | | | | | | | | |
| 1½ | Upp | 3.4 | 7.4 | 5.2 | 3.4 | | | | | | | 4.9 | 4.1 | 1.0 | | | | | | | | | | |
| | | | | | | 36.4 | 54.2 | 23.2 | 14.5 | 13.8 | 11.6 | | | | 2.0 | 5.6 | 7.2 | 6.1 | 4.4 | 2.6 | 1.4 | 0.8 | 1.0 | 1.1 |
| | Low | 7.0 | 4.9 | 3.4 | 7.0 | | | | | | | 4.9 | 4.1 | 1.0 | | | | | | | | | | |
| 2 | Upp | 3.5 | 7.5 | 5.3 | 3.5 | | | | | | | 5.0 | 4.2 | 1.0 | | | | | | | | | | |
| | | | | | | 37.5 | 55.1 | 24.0 | 14.8 | 14.1 | 11.8 | | | | 2.0 | 5.7 | 7.3 | 6.2 | 4.5 | 2.7 | 1.5 | 0.8 | 1.0 | 1.1 |
| | Low | 7.2 | 5.1 | 3.5 | 7.2 | | | | | | | 5.0 | 4.2 | 1.0 | | | | | | | | | | |
| 2½ | Upp | 3.5 | 7.7 | 5.5 | 3.5 | | | | | | | 5.0 | 4.2 | 1.0 | | | | | | | | | | |
| | | | | | | 38.5 | 56.1 | 24.7 | 15.0 | 14.3 | 12.1 | | | | 2.0 | 5.8 | 7.4 | 6.2 | 4.6 | 2.7 | 1.5 | 0.9 | 1.1 | 1.2 |
| | Low | 7.3 | 5.1 | 3.6 | 7.3 | | | | | | | 5.0 | 4.2 | 1.0 | | | | | | | | | | |
| 3 | Upp | 3.6 | 7.8 | 5.7 | 3.6 | | | | | | | 5.0 | 4.2 | 1.1 | | | | | | | | | | |
| | | | | | | 39.6 | 57.0 | 25.4 | 15.2 | 14.5 | 12.3 | | | | 2.0 | 5.9 | 7.5 | 6.3 | 4.7 | 2.8 | 1.6 | 1.0 | 1.1 | 1.3 |
| | Low | 7.5 | 5.3 | 3.8 | 7.5 | | | | | | | 5.0 | 4.2 | 1.1 | | | | | | | | | | |
| 3½ | Upp | 3.6 | 8.0 | 5.7 | 3.6 | | | | | | | 5.1 | 4.3 | 1.1 | | | | | | | | | | |
| | | | | | | 40.6 | 58.0 | 26.1 | 15.4 | 14.7 | 12.5 | | | | 2.0 | 6.1 | 7.6 | 6.3 | 4.7 | 2.8 | 1.6 | 1.0 | 1.2 | 1.3 |
| | Low | 7.7 | 5.4 | 3.8 | 7.7 | | | | | | | 5.1 | 4.3 | 1.1 | | | | | | | | | | |
| 4 | Upp | 3.7 | 8.2 | 6.0 | 3.7 | | | | | | | 5.1 | 4.3 | 1.1 | | | | | | | | | | |
| | | | | | | 41.6 | 59.0 | 26.9 | 15.6 | 14.9 | 12.8 | | | | 2.0 | 6.2 | 7.7 | 6.4 | 4.9 | 2.9 | 1.7 | 1.1 | 1.2 | 1.4 |
| | Low | 7.9 | 5.5 | 4.0 | 7.9 | | | | | | | 5.1 | 4.3 | 1.1 | | | | | | | | | | |
| 4½ | Upp | 3.7 | 8.4 | 6.2 | 3.7 | | | | | | | 5.1 | 4.3 | 1.1 | | | | | | | | | | |
| | | | | | | 42.7 | 60.0 | 27.6 | 15.9 | 15.2 | 13.0 | | | | 2.0 | 6.3 | 7.8 | 6.4 | 5.0 | 3.0 | 1.7 | 1.2 | 1.3 | 1.5 |
| | Low | 8.0 | 5.6 | 4.2 | 8.0 | | | | | | | 5.1 | 4.3 | 1.1 | | | | | | | | | | |
| 5 | Upp | 3.8 | 8.5 | 6.3 | 3.8 | | | | | | | 5.2 | 4.4 | 1.1 | | | | | | | | | | |
| | | | | | | 43.7 | 60.9 | 28.3 | 16.1 | 15.4 | 13.2 | | | | 2.0 | 6.4 | 7.9 | 6.5 | 5.2 | 3.0 | 1.8 | 1.2 | 1.4 | 1.5 |
| | Low | 8.2 | 5.7 | 4.2 | 8.2 | | | | | | | 5.2 | 4.4 | 1.1 | | | | | | | | | | |
| 5½ | Upp | 3.8 | 8.7 | 6.5 | 3.8 | | | | | | | 5.2 | 4.4 | 1.2 | | | | | | | | | | |
| | | | | | | 44.8 | 61.8 | 29.1 | 16.3 | 15.6 | 13.4 | | | | 2.0 | 6.6 | 8.0 | 6.5 | 5.2 | 3.1 | 1.8 | 1.3 | 1.4 | 1.6 |
| | Low | 8.4 | 5.8 | 7.4 | 8.4 | | | | | | | 5.2 | 4.4 | 1.2 | | | | | | | | | | |
| 6 | Upp | 3.9 | 8.9 | 6.8 | 3.8 | | | | | | | 5.2 | 4.4 | 1.2 | | | | | | | | | | |
| | | | | | | 45.8 | 62.8 | 29.8 | 16.5 | 15.8 | 13.7 | | | | 2.0 | 6.7 | 8.1 | 6.6 | 5.4 | 3.1 | 1.9 | 1.4 | 1.5 | 1.7 |
| | Low | 8.6 | 5.9 | 4.5 | 8.6 | | | | | | | 5.2 | 4.4 | 1.2 | | | | | | | | | | |

TABLE II

GROSS DIMENSIONS FOR CLOSELY ADAPTED RETAINER
Extraction
in m.m.

| Size | | a | b | c | d | e | f | g | h | i | j | k | l | m | n | o | p | q | r | s | t | v | w | x |
|---|---|---|---|---|---|---|---|---|---|---|---|---|---|---|---|---|---|---|---|---|---|---|---|---|
| 1 | Upp | 3.6 | 6.3 | 5.7 | 3.6 | | | | | | | 5.0 | 4.2 | 1.1 | | | | | | | | | | |
| | | | | | | 37.8 | 55.0 | 20.3 | 15.2 | 14.5 | 12.3 | | | | 2.0 | 5.9 | 7.5 | 6.3 | 4.7 | 2.8 | 1.6 | 1.0 | 1.1 | 1.3 |
| | Low | 7.5 | 4.2 | 3.8 | 7.5 | | | | | | | 5.0 | 4.2 | 1.1 | | | | | | | | | | |
| 1½ | Upp | 3.6 | 6.5 | 5.7 | 3.6 | | | | | | | 5.1 | 4.3 | 1.1 | | | | | | | | | | |
| | | | | | | 38.8 | 55.9 | 20.8 | 15.4 | 14.7 | 12.5 | | | | 2.0 | 6.1 | 7.6 | 6.3 | 4.7 | 2.8 | 1.6 | 1.0 | 1.2 | 1.3 |
| | Low | 7.7 | 4.8 | 3.8 | 7.7 | | | | | | | 5.1 | 4.3 | 1.1 | | | | | | | | | | |
| 2 | Upp | 3.7 | 6.6 | 6.0 | 3.7 | | | | | | | 5.1 | 4.3 | 1.1 | | | | | | | | | | |
| | | | | | | 39.8 | 56.8 | 21.4 | 15.6 | 14.9 | 12.8 | | | | 2.0 | 6.2 | 7.7 | 6.4 | 4.9 | 2.9 | 1.7 | 1.1 | 1.2 | 1.4 |
| | Low | 7.9 | 4.5 | 4.0 | 7.9 | | | | | | | 5.1 | 4.3 | 1.1 | | | | | | | | | | |
| 2½ | Upp | 3.7 | 6.8 | 6.2 | 3.7 | | | | | | | 5.1 | 4.3 | 1.1 | | | | | | | | | | |
| | | | | | | 40.8 | 57.7 | 21.9 | 15.9 | 15.2 | 13.0 | | | | 2.0 | 6.3 | 7.8 | 6.4 | 5.0 | 3.0 | 1.7 | 1.2 | 1.3 | 1.5 |
| | Low | 8.0 | 4.6 | 4.2 | 8.0 | | | | | | | 5.1 | 4.3 | 1.1 | | | | | | | | | | |
| 3 | Upp | 3.8 | 7.1 | 6.3 | 3.8 | | | | | | | 5.2 | 4.4 | 1.1 | | | | | | | | | | |
| | | | | | | 41.8 | 58.6 | 22.5 | 16.1 | 15.4 | 13.2 | | | | 2.0 | 6.4 | 7.9 | 6.5 | 5.2 | 3.0 | 1.8 | 1.2 | 1.4 | 1.5 |
| | Low | 8.2 | 4.7 | 4.2 | 8.2 | | | | | | | 5.2 | 4.4 | 1.1 | | | | | | | | | | |
| 3½ | Upp | 3.8 | 7.2 | 6.5 | 3.8 | | | | | | | 5.2 | 4.4 | 1.2 | | | | | | | | | | |
| | | | | | | 42.7 | 59.5 | 23.0 | 16.3 | 15.6 | 13.4 | | | | 2.0 | 6.6 | 8.0 | 6.5 | 5.2 | 3.1 | 1.8 | 1.3 | 1.4 | 1.6 |
| | Low | 8.4 | 4.9 | 4.4 | 8.4 | | | | | | | 5.2 | 4.4 | 1.2 | | | | | | | | | | |
| 4 | Upp | 3.9 | 7.4 | 6.8 | 3.9 | | | | | | | 5.2 | 4.4 | 1.2 | | | | | | | | | | |
| | | | | | | 43.7 | 60.4 | 23.5 | 16.5 | 15.8 | 13.7 | | | | 2.0 | 6.7 | 8.1 | 6.6 | 5.4 | 3.1 | 1.9 | 1.4 | 1.5 | 1.7 |
| | Low | 8.6 | 5.0 | 4.5 | 8.6 | | | | | | | 5.2 | 4.4 | 1.2 | | | | | | | | | | |
| 4½ | Upp | 3.9 | 7.6 | 6.9 | 3.9 | | | | | | | 5.3 | 4.5 | 1.2 | | | | | | | | | | |
| | | | | | | 44.7 | 61.3 | 24.1 | 16.7 | 16.0 | 13.9 | | | | 2.0 | 6.9 | 8.2 | 6.6 | 5.5 | 3.2 | 1.9 | 1.4 | 1.5 | 1.7 |
| | Low | 8.8 | 5.1 | 4.6 | 8.8 | | | | | | | 5.3 | 4.5 | 1.2 | | | | | | | | | | |
| 5 | Upp | 4.0 | 7.8 | 7.1 | 4.0 | | | | | | | 5.3 | 4.5 | 1.2 | | | | | | | | | | |

TABLE II-continued
GROSS DIMENSIONS FOR CLOSELY ADAPTED RETAINER
Extraction in m.m.

| Size | | a | b | c | d | e | f | g | h | i | j | k | l | m | n | o | p | q | r | s | t | v | w | x |
|---|---|---|---|---|---|---|---|---|---|---|---|---|---|---|---|---|---|---|---|---|---|---|---|---|
| 5½ | Low | 8.9 | 5.2 | 4.7 | 8.9 | 45.7 | 62.2 | 24.6 | 17.0 | 16.3 | 14.1 | 5.3 | 4.5 | 1.2 | 2.0 | 6.9 | 8.3 | 6.7 | 5.6 | 3.2 | 2.0 | 1.5 | 1.6 | 1.8 |
|  | Upp | 4.0 | 8.0 | 7.3 | 4.0 |  |  |  |  |  |  | 5.3 | 4.5 | 1.3 |  |  |  |  |  |  |  |  |  |  |
| 6 | Low | 9.1 | 5.3 | 4.9 | 9.1 | 46.7 | 63.1 | 25.2 | 17.2 | 16.6 | 14.4 | 5.3 | 4.5 | 1.3 | 2.0 | 7.1 | 8.4 | 6.7 | 5.7 | 3.3 | 2.0 | 1.6 | 1.6 | 1.9 |
|  | Upp | 4.1 | 8.1 | 7.4 | 4.1 |  |  |  |  |  |  | 5.4 | 4.6 | 1.3 |  |  |  |  |  |  |  |  |  |  |
|  | Low | 9.2 | 5.5 | 5.0 | 9.2 | 47.7 | 64.0 | 25.7 | 17.4 | 16.7 | 14.6 | 5.4 | 4.6 | 1.3 | 2.0 | 7.1 | 8.5 | 6.8 | 5.8 | 3.4 | 2.1 | 1.6 | 1.7 | 1.9 |

TABLE III
FURTHER DIMENSIONS OF NON EXTRACTION CLOSELY ADAPTED RETAINER
MAXILLARY in m.m.

| Size | Incisors (4) Mesio-Distal mm. | Upper Six Anteriors | Canine M-D Diameter | 1st Bic. | 2nd Bic. | 1st Perm. Molar | Canine to Canine Arch-Wdith | 1st Perm. Molar Arch-Width |
|---|---|---|---|---|---|---|---|---|
| 1 | 24.9 | 39.5 | 7.3 | 5.9 | 5.7 | 8.6 | 28.1 | 46.0 |
| 1½ | 26.1 | 41.0 | 7.45 | 6.1 | 5.9 | 8.9 | 28.8 | 46.9 |
| 2 | 27.3 | 42.5 | 7.6 | 6.3 | 6.1 | 9.3 | 29.6 | 47.8 |
| 2½ | 28.4 | 44.0 | 7.8 | 6.5 | 6.2 | 9.6 | 30.3 | 48.6 |
| 3 | 29.6 | 45.5 | 7.95 | 6.7 | 6.4 | 10.0 | 21.1 | 49.5 |
| 3½ | 30.8 | 47.0 | 8.1 | 6.8 | 6.6 | 10.3 | 31.8 | 50.4 |
| 4 | 32.0 | 48.5 | 8.25 | 7.0 | 6.8 | 10.7 | 32.6 | 51.3 |
| 4½ | 33.2 | 50.0 | 8.4 | 7.2 | 7.0 | 11.0 | 33.3 | 52.2 |
| 5 | 34.3 | 51.5 | 8.6 | 7.4 | 7.1 | 11.4 | 34.1 | 53.0 |
| 5½ | 35.5 | 53.0 | 8.75 | 7.6 | 7.3 | 11.7 | 34.8 | 53.9 |
| 6 | 36.7 | 54.5 | 8.9 | 7.8 | 7.5 | 12.1 | 35.6 | 54.8 |

MANIDBULAR in mm.

| Size | Incisors (4) Mesio-Distal mm. | Upper Six Anteriors | Canine M-D Diameter | 1st Bic. | 2nd Bic. | 1st Perm. Molar | Canine to Canine Arch-Wdith | 1st Perm. Molar Arch-Width |
|---|---|---|---|---|---|---|---|---|
| 1 | 18.9 | 24.7 | 5.79 | 6.9 | 6.9 | 9.0 | 22.6 | 41.2 |
| 1½ | 19.7 | 25.7 | 5.97 | 6.2 | 6.2 | 9.4 | 23.2 | 42.0 |
| 2 | 20.5 | 26.7 | 6.15 | 6.5 | 6.5 | 9.7 | 23.8 | 42.8 |
| 2½ | 21.2 | 27.6 | 6.4 | 6.6 | 6.6 | 10.1 | 24.4 | 43.5 |
| 3 | 22.0 | 28.6 | 6.6 | 6.8 | 6.8 | 10.5 | 25.0 | 44.3 |
| 3½ | 22.8 | 29.5 | 6.7 | 7.0 | 7.0 | 10.8 | 25.6 | 45.2 |
| 4 | 23.6 | 30.5 | 6.9 | 7.2 | 7.2 | 11.2 | 26.3 | 46.0 |
| 4½ | 24.4 | 31.5 | 7.1 | 7.3 | 7.3 | 11.2 | 26.3 | 46.0 |
| 5 | 25.1 | 32.4 | 7.3 | 7.6 | 7.6 | 12.0 | 27.5 | 47.5 |
| 5½ | 25.9 | 33.4 | 7.5 | 7.7 | 7.7 | 12.3 | 28.1 | 48.3 |
| 6 | 26.7 | 34.4 | 7.7 | 8.0 | 8.0 | 12.7 | 28.7 | 49.1 |

TABLE IV
FURTHER DIMENSIONS OF EXTRACTION CLOSELY ADAPTED RETAINER
MAXILLARY in m.m.

| Size | Incisors (4) Mesio-Distal mm. | Upper Six Anteriors | Canine M-D Diameter | 2nd. Bic. | 1st. Perm. Molar | Canine to Canine Arch-Width | 1st Perm. Molar Arch-Width |
|---|---|---|---|---|---|---|---|
| 1 | 29.6 | 45.5 | 7.95 | 6.4 | 10.0 | 31.1 | 49.5 |
| 1½ | 30.8 | 47.0 | 8.1 | 6.6 | 10.3 | 31.8 | 50.4 |
| 2 | 32.0 | 48.5 | 8.25 | 6.8 | 10.7 | 32.6 | 51.3 |
| 2½ | 33.2 | 50.0 | 8.4 | 7.0 | 11.0 | 33.3 | 52.2 |
| 3 | 34.3 | 51.5 | 8.6 | 7.1 | 11.4 | 34.1 | 53.0 |
| 3½ | 35.5 | 53.0 | 8.75 | 7.3 | 11.7 | 34.8 | 53.9 |
| 4 | 36.7 | 54.5 | 8.9 | 7.5 | 12.1 | 35.6 | 54.8 |
| 4½ | 37.9 | 56.0 | 9.1 | 7.7 | 12.4 | 36.3 | 55.7 |
| 5 | 39.1 | 57.5 | 9.2 | 7.8 | 12.8 | 37.1 | 56.6 |
| 5½ | 40.3 | 59.0 | 9.4 | 8.0 | 13.1 | 37.8 | 57.4 |
| 6 | 40.5 | 60.5 | 9.5 | 8.2 | 13.5 | 38.6 | 58.3 |

MANDIBULAR in mm.

| Size | Incisors (4) Mesio-Distal mm. | Upper Six Anteriors | Canine M-D Diameter | 2nd. Bic. | 1st. Perm. Molar | Canine to Canine Arch-Width | 1st Perm. Molar Arch-Width |
|---|---|---|---|---|---|---|---|
| 1 | 22.0 | 28.6 | 6.6 | 6.8 | 10.5 | 25.0 | 44.3 |
| 1½ | 22.8 | 29.5 | 6.7 | 7.0 | 10.8 | 25.6 | 45.2 |
| 2 | 23.6 | 30.5 | 6.9 | 7.2 | 11.2 | 26.3 | 46.0 |
| 2½ | 24.4 | 31.5 | 7.1 | 7.3 | 11.6 | 26.9 | 46.8 |
| 3 | 25.1 | 32.4 | 7.3 | 7.6 | 12.0 | 27.5 | 47.5 |
| 3½ | 25.9 | 33.4 | 7.5 | 7.7 | 12.3 | 28.1 | 48.3 |
| 4 | 26.7 | 34.4 | 7.7 | 8.0 | 12.7 | 28.7 | 49.1 |
| 4½ | 27.5 | 35.3 | 7.9 | 8.2 | 13.1 | 29.3 | 49.9 |
| 5 | 28.3 | 36.3 | 8.1 | 8.4 | 13.5 | 29.9 | 50.7 |
| 5½ | 29.0 | 37.3 | 8.3 | 8.6 | 13.9 | 30.6 | 51.5 |
| 6 | 29.8 | 38.2 | 8.5 | 8.8 | 14.2 | 31.2 | 52.3 |

Although the invention has been described in considerable detail, it will be apparent that the invention is capable of numerous modifications and variations which will be apparent to those skilled in the art without departing from the spirit or scope of the invention.

I claim:

1. An orthodontic appliance of the type which is generally U-shaped in plan view and which includes a tooth receiving trough for at least one of the upper or lower row of a patient's teeth, said trough being formed between a labial-buccal flange and a lingual flange, said appliance being formed of a material which can be softened and non-elastically reshaped at a softening temperature which is located between 100° and 212° F, and which, below the softening temperature, is relatively hard, stiff and essentially non-resilient, said appliance, after being reshaped, exactly fitting the teeth of a given patient at least in the area of the occlusal and incisal edges of a row of teeth and from the occlusal or incisal edges thereof to the undercut portion of the clinical crown surfaces of at least some of the teeth of that row, said material, thus exactly fitting said teeth, being capable of snapping into place onto the said row of teeth to hold the patient's teeth in that position which it exactly fits.

2. An orthodontic appliance according to claim 1, said appliance being a maxillary appliance for fitting a patient's upper teeth.

3. An orthodontic appliance according to claim 2, said flanges extending generally to the gingival edges of the teeth except for that portion of the labial-buccal flange at the anterior teeth which extend up for approximately one-third the distance from the incisal edges to the gingival edges of those anterior teeth.

4. An orthodontic appliance according to claim 3, including a labial wire formed in the appliance and extending across the front of the upper anterior teeth.

5. An orthodontic appliance according to claim 3, including a hook means extending out from the outer surface of the labial flange for receiving an elastic band stretched across the front of the appliance.

6. An orthodontic appliance according to claim 2, the thickness of the appliance at the occlusal edges at the bottom thereof being approximately 2 mm thick in the posterior region and approximately 3 mm at the anterior region.

7. An orthodontic appliance according to claim 2, the bottom of the appliance being generally plain and including slight indentations therein for the tops of some bottom teeth as required to cause all of the patient's bottom teeth to engage the bottom surface of the appliance essentially concurrently.

8. An orthodontic appliance according to claim 1, said appliance being a mandibular appliance for fitting a patient's lower teeth.

9. An orthodontic appliance according to claim 8, said flanges extending generally to the gingival edges of the teeth except for that portion of the labial-buccal flange at the anterior teeth which extend downwardly for approximately one-half the distance from the incisal edges to the gingival edges of those anterior teeth.

10. An orthodontic appliance according to claim 8, the thickness of the appliance at the occlusal edges at the top thereof being approximately 2 mm thick in the posterior region and approximately 3 mm thick at the anterior region.

11. An orthodontic appliance according to claim 8, the top of the appliance being generally plain and including slight indentations therein for the bottoms of some upper teeth as required to cause all of the patient's upper teeth to engage the upper surface of the appliance essentially concurrently.

12. An orthodontic appliance according to claim 1, including a pair of appliances, one for the patient's upper teeth and one for the patient's lower teeth, and including means for removably attaching these appliances together within the patient's mouth.

13. An orthdontic appliance according to claim 12, said means for removably attaching the appliances including a projection on one of the appliances resiliently engagable in a recess in the other appliance.

14. An orthodontic appliance according to claim 1, said lingual and labial-buccal flanges extending a distance sufficient to reach the gingival edges of a patient's teeth.

15. An orthodontic appliance according to claim 1, said appliance including a single trough which is for the upper teeth, and including a generally plain lower surface for engaging the occlusal edges of the lower teeth.

16. An orthodontic appliance according to claim 15, including a hook means extending out from the outer surface of the labial flange for receiving an elastic band stretched across the front of the appliance.

17. An orthodontic appliance according to claim 15, including means on the lower surface of the appliance for cooperating with a similar appliance for the lower teeth for fixed attachment of the two appliances to each other.

18. A set of appliances according to claim 1, said set comprising a limited number of different size appliances which in toto fit substantially the entire orthodontic patient population.

19. An orthodontic appliance according to claim 1, said appliance including a single trough which is for the lower teeth, and including a generally plain upper surface for engaging the occlusal surface of the upper teeth.

20. An orthodontic appliance according to claim 19, including means on the upper surface of the appliance for cooperating with a similar appliance for the upper teeth for fixed attachment of the two appliances with each other.

21. A set of appliances according to claim 1, said set comprising a limited number of different size appliances which in toto fits substantially the entire orthodontic patient population, said appliances having the dimensions according to Tables I to IV.

22. A method of forming an appliance for orthodontically treating a patient to hold certain teeth in a certain selected position, comprising the steps of:

taking a performed appliance which is generally U-shaped in plan view and which includes a tooth receiving trough formed between a labial-buccal flange and a lingual flange for receiving at least one of the upper and lower row of teeth, said appliance being of a hard, stiff essentially non-resilient material capable of softening and being non-elastically reshaped at a softening temperature located between 100° and 212° F, heating the appliance to its softening temperature and while soft, placing it in the patient's mouth and reshaping it to the exact shape of at least a portion of at least some of the patient's teeth of that row from the occlusal or incisal edges thereof to the undercut portions of the clinical crown surfaces thereof, and cooling the appliance below said softening temperature such that it again becomes hard, stiff and essentially non-resilient such that it can snap into place on those teeth which it fits to hold those teeth in that precise position.

23. A method according to claim 22, including performing said cooling step, at least initially, while the appliance remains in the patient's mouth fitted onto the patient's teeth, until the appliance becomes slightly stiff.

24. A method according to claim 23, including removing the appliance from the patient's mouth after it has become slightly stiff, trimming the flanges back to at least the gingival edges of the teeth, and then reinserting the appliance into the patient's mouth onto the patient's teeth to check the abiliby of the appliance to remain on the patient's teeth.

25. A method according to claim 22, including, after said cooling step, trimming back the flanges to a height corresponding to the gingival edges of the patient's teeth.

26. A method according to claim 25, wherein the appliance is a maxillary appliance for the patient's upper teeth and the trimming step includes additionally trimming back the labial-buccal flange in the vicinity of the anterior teeth to a height equal to one-third the labial surface of those teeth.

27. A method according to claim 25, wherein the appliance is a mandibular appliance for the lower teeth and trimming step includes additionally trimming back the labial-buccal flange in the vicinity of the anterior teeth to a height equal to one-half the labial surface of those teeth.

28. A method according to claim 22, said appliance having only one trough, and said reshaping step includes reshaping the outer surface of the appliance across from the bottom of the trough to mate with the occlusal edges of the opposite row of teeth, such that the occlusal edges of said opposite row of teeth all engage the outer side of the appliance essentially concurrently with each other.

29. A method according to claim 22, said taking step further including selecting a proper size preformed appliance from a set of a limited number thereof, which set, in toto, fits essentially the entire orthodontic dental patient population.

30. A method of forming an appliance for orthodontically treating a patient to hold certain teeth in a certain selected position, comprising the steps of: taking a body of material which is of a hard, stiff, essentially non-resilient material capable of softening and being non-elastically reshaped at a softening temperature located between 100° and 212° F, heating the appliance to its softening temperature and while soft, placing the body of material in the patient's mouth and reshaping it to the exact shape of a portion of at least some of the teeth of at least one of the upper and lower rows of the patient's teeth, such that the resultant appliance is generally U-shaped in plan view with a trough shaped to exactly fit said teeth formed between a labial-buccal flange and a lingual flange connected by a isthmus, the flanges of the trough extending from the occlusal or incisal edges of the teeth of that row to the undercut portions of the clinical crown surfaces of at least some teeth of that row, and cooling the appliance below said softening temperature such that it again becomes hard, stiff and essentially non-resilient and can snap onto those teeth which it fits.

31. A method according to claim 30, including performing said cooling step, at least initially, while the appliance remains in the patient's mouth fitted onto the patient's teeth, until the appliance becomes slightly stiff.

32. A method according to claim 31, including removing the appliance from the patient's mouth after it has become slightly stiff, trimming the flanges back to at least the gingival edges of the teeth, and then reinserting the appliance into the patient's mouth onto the patient's teeth to check the ability of the appliance to remain on the patient's teeth.

33. A method according to claim 30, including, after said cooling step, trimming back the flanges to a height corresponding to the gingival edges of the patient's teeth.

34. A method according to claim 33, wherein the appliance is a maxillary appliance for the patient's upper teeth and the trimming step includes additionally trimming back the labial-buccal flange in the vicinity of the anterior teeth to a height equal to one-third the labial surface of those teeth.

35. A method according to claim 33, wherein the appliance is a mandibular appliance for the lower teeth and trimming step includes additionally trimming back the labial-buccal flange in the vicinity of the anterior teeth to a height equal to one-half the labial surface of those teeth.

36. A method according to claim 30, said appliance having only one trough, and said reshaping step includes reshaping the outer surface of the appliance across from the bottom of the trough to mate with the occlusal edges of the opposite row of teeth, such that the occlusal edges of said opposite row of teeth all engage the outer side of the appliance essentially concurrently with each other.

* * * * *